(12) United States Patent
Nixon et al.

(10) Patent No.: US 11,642,939 B2
(45) Date of Patent: May 9, 2023

(54) SYSTEM FOR DISTRIBUTING VOLATILE SUBSTANCE WITH BASE UNIT AND SELF-SEALING REMOVABLE CAPSULE

(71) Applicant: Henkel AG & Co. KGaA, Duesseldorf (DE)

(72) Inventors: Anne Elizabeth Lindert Nixon, La Grange, KY (US); Daniel Nelsen, Central Falls, RI (US); Glenn W. Kaye, Norwalk, CT (US); Artem O. Kirshon, Plainsboro, NJ (US); Kevin M. Hafer, Shoreline, WA (US); Terannie Vazquez Alvarez, East Orange, CT (US); Jamie Scott Anderson, Sandy Hook, CT (US); Martin Haupt, Vienna (AT); Jonathan Rolland, San Diego, CA (US); Pau Mauri Piñol, L'Aldea (ES); Roman Prager, Vienna (AT); Ismael Castellvi Anguera, L'Aldea (ES); Joan Marc Escudero Vericat, L'Aldea (ES); Amanda Williams, San Jose, CA (US); Alex Dupont, Waltham, MA (US)

(73) Assignee: Henkel AG & Co. KGaA, Duesseldorf (DE)

( * ) Notice: Subject to any disclaimer, the term of this patent is extended or adjusted under 35 U.S.C. 154(b) by 571 days.

(21) Appl. No.: 16/785,474

(22) Filed: Feb. 7, 2020

(65) Prior Publication Data

US 2020/0254130 A1 Aug. 13, 2020

Related U.S. Application Data

(60) Provisional application No. 62/802,980, filed on Feb. 8, 2019, provisional application No. 62/802,997, filed
(Continued)

(51) Int. Cl.
*A61L 9/12* (2006.01)
*B60H 3/00* (2006.01)
(Continued)

(52) U.S. Cl.
CPC ............ *B60H 3/0007* (2013.01); *A61L 9/122* (2013.01); *B05B 11/0054* (2013.01);
(Continued)

(58) Field of Classification Search
None
See application file for complete search history.

(56) References Cited

U.S. PATENT DOCUMENTS 3,993,444 A 11/1976 Brown
4,035,451 A 7/1977 Tringali
(Continued)

FOREIGN PATENT DOCUMENTS

EP 0800832 A1 10/1997
KR 2020090008236 U 8/2009
(Continued)

OTHER PUBLICATIONS

International Search Report and Written Opinion PCT/US2020/017394 Completion Date: Jun. 4, 2020; dated Jun. 4, 2020 pp. 10.
(Continued)

*Primary Examiner* — Jelitza M Perez
(74) *Attorney, Agent, or Firm* — Bojuan Deng (57) ABSTRACT

A capsule of a volatile substance distribution system is configured for use with a base unit having a fan and an air outlet configured to direct air driven by the fan away from the base unit. The capsule includes a housing that extends along a longitudinal axis between a first end and a second end. The first end defines an inlet port and the second end defines an outlet port. The housing houses a volatile substance member. The capsule further includes an outlet seal
(Continued)

member that seals and unseals the outlet port. The housing, when engaged with the base unit and with the outlet seal member in the unsealed position, is configured to receive the air from the air outlet that flows into the inlet port, past the volatile substance member, and out of the outlet port.

19 Claims, 8 Drawing Sheets

Related U.S. Application Data on Feb. 8, 2019, provisional application No. 62/803,010, filed on Feb. 8, 2019, provisional application No. 62/803,020, filed on Feb. 8, 2019, provisional application No. 62/803,034, filed on Feb. 8, 2019.

(51) Int. Cl.
| | |
|---|---|
| *B05B 12/02* | (2006.01) |
| *B05B 11/00* | (2023.01) |
| *B05B 11/06* | (2006.01) |
| *A61L 9/02* | (2006.01) |
| *A01M 1/20* | (2006.01) |

(52) U.S. Cl.
CPC ............. *B05B 11/06* (2013.01); *B05B 12/02* (2013.01); *A01M 1/2033* (2013.01); *A61L 9/02* (2013.01); *A61L 2209/11* (2013.01); *A61L 2209/133* (2013.01); *B60H 2003/005* (2013.01); *B60H 2003/0042* (2013.01)

(56) References Cited

U.S. PATENT DOCUMENTS

| | | | |
|---|---|---|---|
| 4,065,261 A | 12/1977 | Fukada | |
| 4,111,655 A | 9/1978 | Quincey | |
| 4,173,604 A | 11/1979 | Dimacopoulos | |
| 4,271,092 A | 6/1981 | Sullivan et al. | |
| 4,294,778 A | 10/1981 | DeLuca | |
| 4,301,095 A | 11/1981 | Mettler et al. | |
| 4,383,951 A | 5/1983 | Palson | |
| 4,432,938 A | 2/1984 | Meetze, Jr. | |
| 5,012,961 A | 5/1991 | Madsen et al. | |
| 5,126,078 A | 6/1992 | Steiner et al. | |
| 5,234,162 A | 8/1993 | Sullivan | |
| 5,335,446 A | 8/1994 | Shigetoyo | |
| 5,547,616 A | 8/1996 | Dancs et al. | |
| 5,662,835 A | 9/1997 | Collingwood | |
| 5,820,792 A | 10/1998 | Lin | |
| 5,932,147 A | 8/1999 | Chen | |
| 6,050,551 A | 4/2000 | Anderson | |
| 6,390,453 B1 | 5/2002 | Frederickson et al. | |
| 6,443,434 B1 | 9/2002 | Prather | |
| 6,569,387 B1 | 5/2003 | Furner et al. | |
| 6,592,104 B2 | 7/2003 | Cox | |
| 6,610,254 B1 | 8/2003 | Furner et al. | |
| 6,719,217 B1 | 4/2004 | Tawara et al. | |
| 6,772,756 B2 | 8/2004 | Shayan | |
| 6,990,978 B2 | 1/2006 | Shayan | |
| 7,011,795 B2 | 3/2006 | Thompson et al. | |
| 7,040,548 B2 | 5/2006 | Rodgers | |
| 7,149,417 B2 | 12/2006 | Joshi et al. | |
| 7,154,579 B2 | 12/2006 | Selander et al. | |
| 7,344,123 B2 | 3/2008 | Pankhurst et al. | |
| 7,377,493 B2 | 5/2008 | Thomas | |
| 7,389,943 B2 | 6/2008 | Jaworski | |
| 7,499,632 B2 | 3/2009 | Granger et al. | |
| 7,527,247 B1 | 5/2009 | Krueger | |
| 7,597,308 B1 | 10/2009 | Stucki | |
| 7,597,309 B1 | 10/2009 | Stucki | |
| 7,691,336 B2 | 4/2010 | Westring | |
| 7,708,256 B2 | 5/2010 | Pankhurst et al. | |
| 7,734,159 B2 | 6/2010 | Beland et al. | |
| 7,748,687 B2 | 7/2010 | Pankhurst et al. | |
| 7,841,587 B2 | 11/2010 | Pankhurst et al. | |
| 7,926,792 B2 | 4/2011 | Pankhurst et al. | |
| 7,962,017 B2 | 6/2011 | Vieira | |
| 8,038,778 B2 | 10/2011 | Chan et al. | |
| 8,043,569 B2 | 10/2011 | Tranzeat | |
| 8,074,970 B2 | 12/2011 | Pankhurst et al. | |
| 8,170,405 B2 | 5/2012 | Harris | |
| 8,196,903 B2 | 6/2012 | Joergensen | |
| 8,211,208 B2 | 7/2012 | Chan et al. | |
| 8,303,697 B2 | 11/2012 | Chan et al. | |
| 8,463,114 B2 | 6/2013 | Garcia Fabrega et al. | |
| 8,498,524 B2 | 7/2013 | Ruiz Ballesteros et al. | |
| 8,556,122 B2 | 10/2013 | Helf et al. | |
| 8,603,397 B2 | 12/2013 | Gruenbacher et al. | |
| 8,632,059 B2 | 1/2014 | Pankhurst et al. | |
| 8,876,086 B2 | 11/2014 | Burke et al. | |
| 8,925,905 B2 | 1/2015 | Vieira | |
| 8,939,435 B2 | 1/2015 | Gordon et al. | |
| 8,983,278 B2 | 3/2015 | Ruiz Ballesteros et al. | |
| 9,061,821 B2 | 6/2015 | Helf et al. | |
| 9,149,031 B2 | 10/2015 | Shi et al. | |
| 9,265,853 B2 | 2/2016 | Scott et al. | |
| 9,352,062 B2 | 5/2016 | Klemm et al. | |
| 9,352,064 B2 | 5/2016 | Furner et al. | |
| 9,393,333 B2 | 7/2016 | Barlow et al. | |
| 9,623,135 B2 | 4/2017 | Joshi et al. | |
| 9,717,815 B2 | 8/2017 | Peterson et al. | |
| 9,895,689 B2 | 2/2018 | Wright et al. | |
| 9,919,070 B2 | 3/2018 | Rappel | |
| 10,058,627 B2 | 8/2018 | Keisen | |
| 10,064,970 B1 | 9/2018 | Shah et al. | |
| 10,137,464 B2 | 11/2018 | Wang et al. | |
| 2004/0033171 A1 | 2/2004 | Kvietok et al. | |
| 2006/0153744 A1 | 7/2006 | Thompson et al. | |
| 2008/0164337 A1 | 7/2008 | Brown et al. | |
| 2010/0176212 A1 | 7/2010 | Ward, Sr. et al. | |
| 2014/0072286 A1 | 3/2014 | Hsiao et al. | |
| 2014/0079586 A1 | 3/2014 | Shapiro et al. | |
| 2015/0328354 A1 | 11/2015 | Guerra et al. | |
| 2016/0375168 A1 | 12/2016 | Hsiao | |
| 2016/0375169 A1 | 12/2016 | Hsiao | |
| 2017/0065737 A1 | 3/2017 | Rappel | |
| 2017/0238527 A1 | 8/2017 | Wynalda, Jr. | |
| 2017/0296689 A1 | 10/2017 | Peterson et al. | |
| 2018/0154036 A1* | 6/2018 | Davis | A61L 9/122 |
| 2018/0169288 A1 | 6/2018 | Kelsen | |
| 2018/0339079 A1 | 11/2018 | Li | |
| 2018/0353636 A1 | 12/2018 | Hafer et al. | |
| 2018/0369442 A1 | 12/2018 | Kelsen | |

FOREIGN PATENT DOCUMENTS

| | | |
|---|---|---|
| KR | 1020130030381 A | 3/2013 |
| WO | 2014032639 A1 | 3/2014 |
| WO | 2017053553 A1 | 3/2017 |
| WO | 2018022562 A1 | 2/2018 |
| WO | 2018081386 A1 | 5/2018 |
| WO | 2018091766 A1 | 5/2018 |

OTHER PUBLICATIONS

Extended European Search Report PCT/US2020017394 Completed date: Oct. 19, 2022; dated Oct. 27, 2022 9 pages.

* cited by examiner

SYSTEM FOR DISTRIBUTING VOLATILE SUBSTANCE WITH BASE UNIT AND SELF-SEALING REMOVABLE CAPSULE

FIELD OF THE INVENTION

The following relates to a volatile substance distribution system and, more particularly, relates to a system for distributing a volatile substance with a base unit and a self-sealing removable capsule.

BACKGROUND OF THE INVENTION

There are various devices used to distribute volatile materials (e.g., perfumes, essential oils, insect repellant, etc.) into the air. Many devices include a unit that supports the volatile material and a fan. The volatile material moves into the airstream moved by the fan for distribution into the air.

However, conventional systems suffer from various drawbacks. For example, many of these devices are bulky. Also, the fan may consume relatively high levels of electricity during use. Moreover, the volatile material may tend to spill or leak from the system. These and other concerns may considerably limit the usefulness of conventional systems. As an example, a conventional system may not be suitable for use in a vehicle because the system may be too big, may require a power cord, may spill volatile material due to movement of the vehicle, etc.

Therefore, there exists a need for a compact volatile material distribution system that consumes minimal amounts of power and that is unlikely to leak volatile material. Other desirable features and characteristics of the devices and methods of the present disclosure will become apparent from the subsequent detailed description and the appended claims, taken in conjunction with the accompanying drawings and the preceding background.

BRIEF SUMMARY OF THE INVENTION

Embodiments of a capsule of a volatile substance distribution system are provided. In various embodiments, the capsule includes a housing that extends along a longitudinal axis between a first end and a second end. The first end defines an inlet port and the second end defines an outlet port. The capsule also includes a volatile substance member that includes a volatile substance. The volatile substance member is contained and supported within the housing. The capsule further includes an outlet seal member disposed proximate the outlet port and configured to selectively move between an unsealed position and a sealed position relative to the outlet port. The outlet seal member substantially seals the outlet port in the sealed position, and the outlet port is unsealed with the outlet seal member in the unsealed position. The housing, with the outlet seal member in the unsealed position, is configured to receive an airflow that flows into the inlet port, past the volatile substance member, and out of the outlet port.

Embodiments of a volatile substance distribution system are also provided. In some embodiments, the system includes a base unit having a base unit housing that supports a fan and that defines an air outlet configured to direct air driven by the fan away from the base unit. The system also includes a capsule configured to be removably supported on the base unit. The capsule includes a housing that extends along a longitudinal axis between a first end and a second end. The first end defines an inlet port and the second end defines an outlet port. The housing is configured to move between an engaged position and a disengaged position relative to the base unit. The housing, in the engaged position, is removably supported on the base unit with the inlet port fluidly connected to the air outlet of the base unit. The housing, in the disengaged position, is spaced apart from the base unit. The capsule further includes a volatile substance member that includes a volatile substance. The volatile substance member is contained and supported within the housing. Moreover, the capsule includes an outlet seal member disposed proximate the outlet port and configured to selectively move between an unsealed position and a sealed position relative to the outlet port. The outlet seal member substantially seals the outlet port in the sealed position. The outlet port is unsealed with the outlet seal member in the unsealed position. The housing, in the engaged position and with the outlet seal member in the unsealed position, is configured to receive the air from the air outlet that flows into the inlet port, past the volatile substance member, and out of the outlet port Methods for manufacturing a volatile substance distribution system are still further provided. In some embodiments, the method includes forming a housing of a capsule that extends along a longitudinal axis between a first end and a second end. The first end defines an inlet port and the second end defining an outlet port. The housing is configured to move between an engaged position and a disengaged position relative to the base unit. The housing, in the engaged position, is removably supported on the base unit with the inlet port fluidly connected to the air outlet of the base unit. The housing, in the disengaged position, is spaced apart from the base unit. Moreover, the method includes providing a volatile substance member that includes a volatile substance within the housing. Furthermore, the method includes supporting an outlet seal member proximate the outlet port and configured to selectively move between an unsealed position and a sealed position relative to the outlet port. The outlet seal member substantially seals the outlet port in the sealed position. The outlet port is unsealed with the outlet seal member in the unsealed position. The housing, in the engaged position and with the outlet seal member in the unsealed position, is configured to receive the air from the air outlet that flows into the inlet port, past the volatile substance member, and out of the outlet port The foregoing statements are provided by way of non-limiting example only. Various additional examples, aspects, and other features of embodiments of the present disclosure are encompassed by the present disclosure and described in more detail below.

BRIEF DESCRIPTION OF THE DRAWINGS

At least one example of the present disclosure will hereinafter be described in conjunction with the following figures, wherein like numerals denote like elements, and.

For simplicity and clarity of illustration, descriptions and details of well-known features and techniques may be omitted to avoid unnecessarily obscuring the exemplary and non-limiting embodiments of the present disclosure described in the subsequent Detailed Description. It should further be understood that features or elements appearing in the accompanying figures are not necessarily drawn to scale unless otherwise stated.

DETAILED DESCRIPTION OF THE INVENTION

The following Detailed Description is merely exemplary in nature and is not intended to limit the present disclosure or the application and uses of the same. The term "exemplary," as appearing throughout this document, is synonymous with the term "example" and is utilized repeatedly below to emphasize that the following description provides only multiple non-limiting examples of the present disclosure and should not be construed to restrict the scope of the present disclosure, as set-out in the claims, in any respect.

Devices for distributing a volatile substance are provided, as are methods for manufacturing such devices. Generally, the devices described herein may include a base unit and a capsule that may be removably supported on the base unit. The capsule may contain a volatile substance member and may receive an airflow that is driven by a fan of the base unit. As the airflow moves through the capsule, the volatile substance may enter the airstream for distribution outside the system.

The capsule and/or the base unit may include various features that enhance the airflow between the base unit and the capsule. For example, in some embodiments, the fan of the base unit may blow air into the capsule via an inlet port. The inlet port and/or other portions of the capsule may be configured to ensure that air from the fan is delivered into the capsule in a predetermined manner. In some embodiments, for example, a lower terminal end of the capsule may removably engage and seat within the base unit, which aligns and fluidly connects the inlet port with an outlet port of the base unit. Additionally, the inlet port may be tapered with respect to a downstream direction of the airflow (e.g., tapered inward radially) to direct the incoming airflow into and through the capsule. Additional features may direct the airflow efficiently and effectively through the capsule and outward to the environment. These and/or other features may increase efficiency of the system, allowing a smaller-duty fan to be used without compromising on performance. Also, these features allow the system to be relatively compact and ergonomic.

Furthermore, in some embodiments, the capsule may include an airflow opening as well as a seal that selectively seals the airflow opening. In some embodiments, the capsule may include an inlet aperture and an inlet seal that selectively seals and unseals the inlet aperture. Furthermore, in some embodiments, the capsule may include an outlet aperture and an outlet seal that selectively seals and unseals the outlet aperture. In some embodiments, the capsule may include each of an inlet aperture with an associated inlet seal as well as an outlet aperture with an associated outlet seal. The inlet aperture and the outlet aperture (as well as the respective seal members) may be substantially centered on a longitudinal axis of the capsule as will be discussed. The seal(s) may be biased toward a sealed position and, therefore, may automatically seal when the fan is OFF and/or when the capsule is removed from the base. In additional embodiments, the base unit and the capsule may include interactive features for mechanically unsealing the capsule when supported on the base and that allow the capsule to automatically re-seal when removed from the base. Furthermore, in some embodiments, the capsule may include a seal that passively opens due to air pressure from the airflow driven by the fan, and that passively biases to a sealed position when the air pressure is reduced (e.g., when the fan is turned OFF). Accordingly, the capsule can be removed from the base and re-used later, or the capsule may be replaced with another capsule with a different scent, etc.

A volatile substance distribution system 100 will now be discussed according to example embodiments illustrated in FIGS. 1-8. Generally, the system 100 includes an upper end 102 and a lower end 104 and a longitudinal axis 106 that extends therebetween. It will be appreciated that the terms "upper" and "lower" are relative terms based on the orientation shown in the Figures and are merely used as an example. Accordingly, the upper end 102 may be referred to as a "first end" and the lower end 104 may be referred to as a "second end." A first radial axis 108 and a second radial axis 109 are also indicated in relation to the longitudinal axis 106 for reference purposes.

Figure 1:
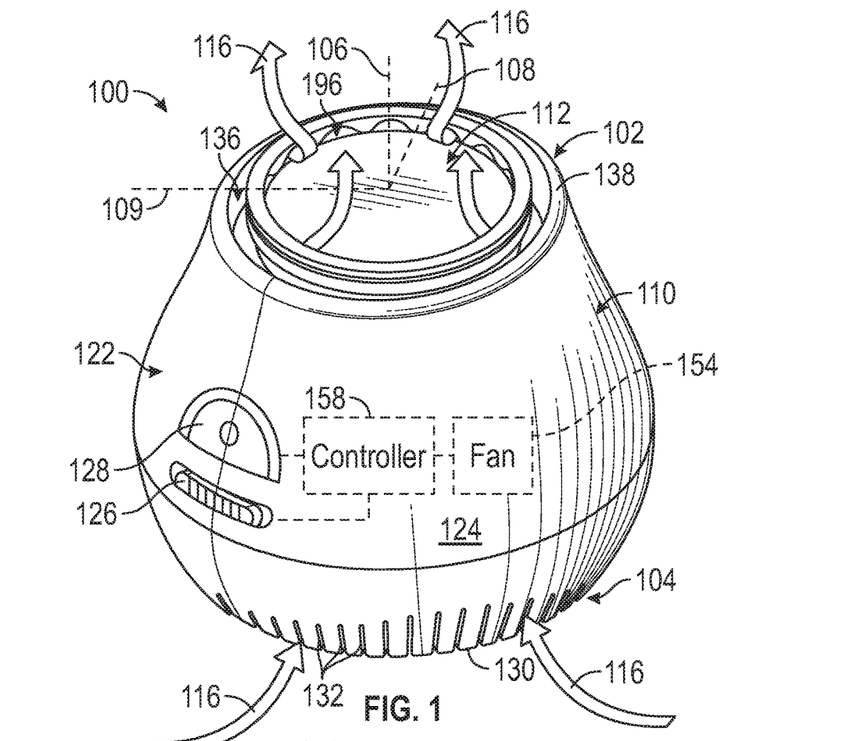
FIG. 1 is a perspective view of a volatile substance distribution system according to example embodiments of the present disclosure.
Figure 2:
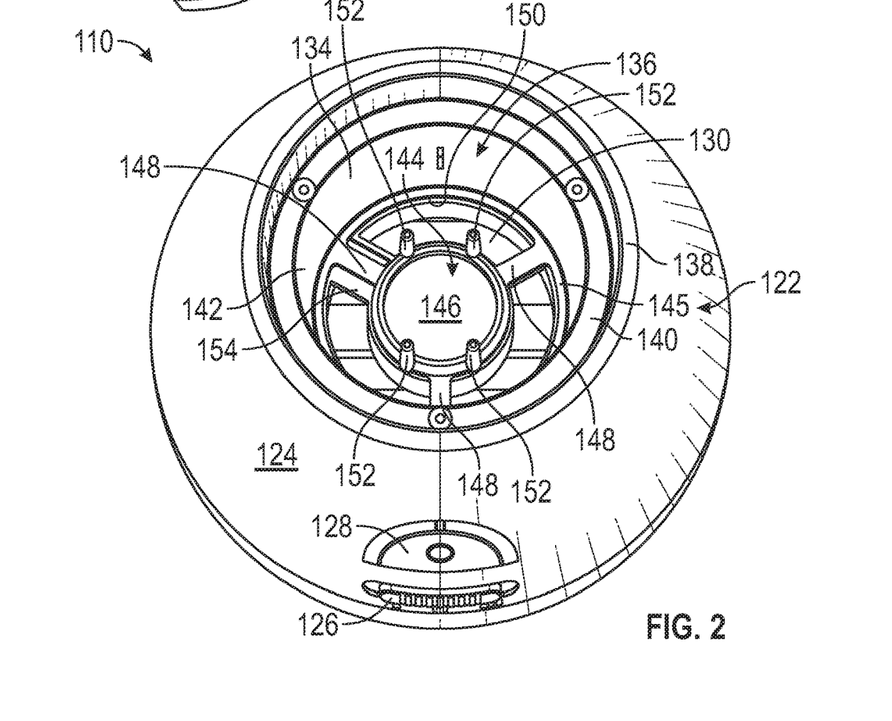
FIG. 2 is a perspective view of a base unit of the system of FIG. 1.
Figure 3:
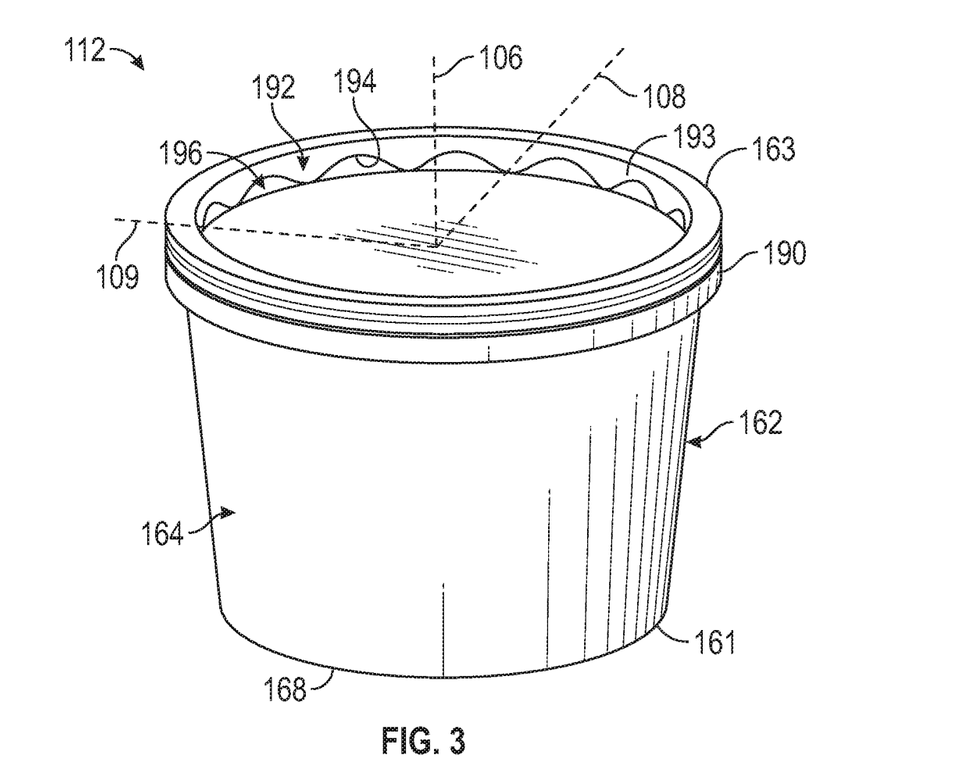
FIG. 3 is a perspective view of a capsule of the system of FIG. 1.
Figure 4:
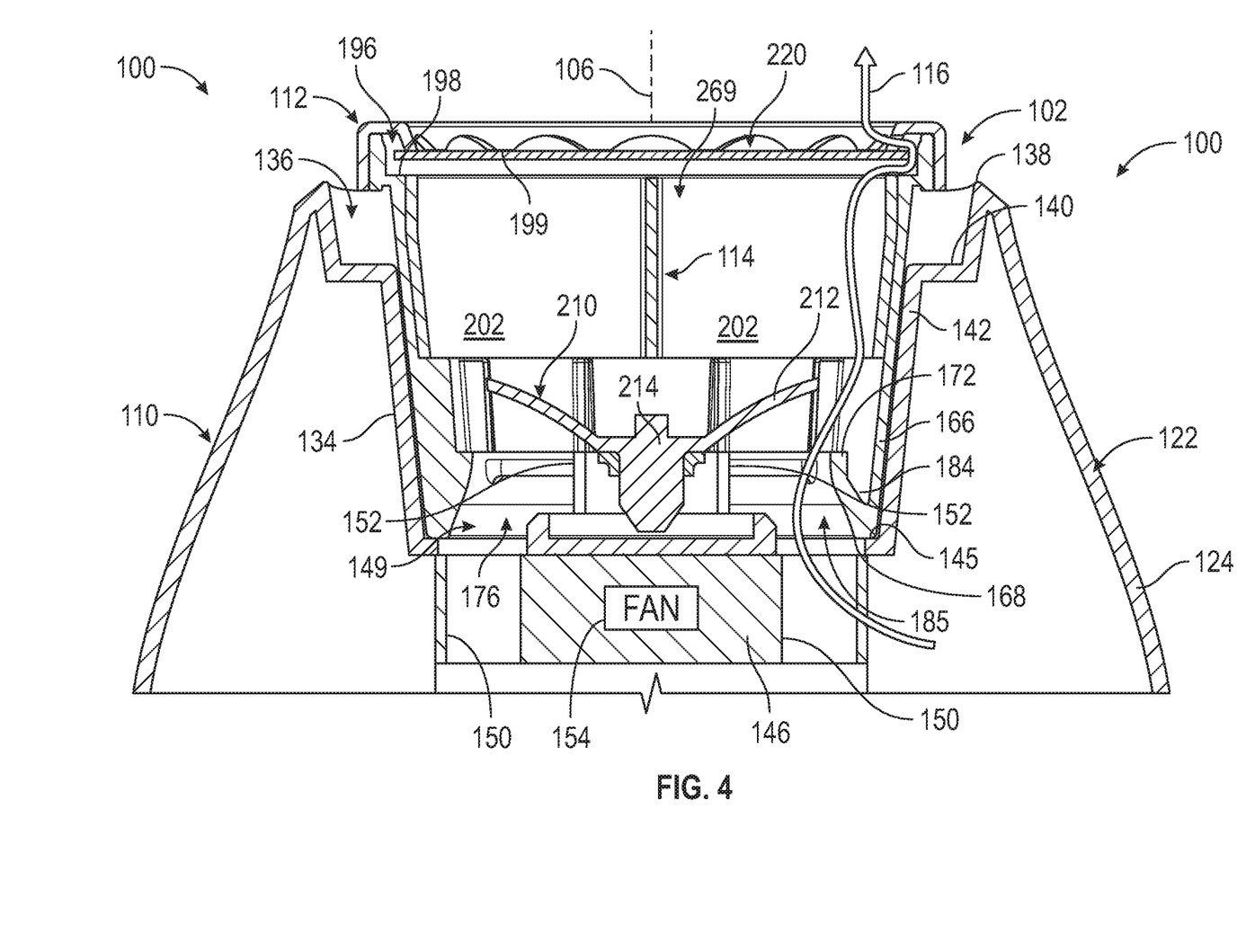
FIG. 4 is a section side view of the base unit and the capsule of the system of FIG. 1.

The volatile substance distribution system 100 may include a base unit 110 (FIGS. 1, 2, and 4) and a volatile substance capsule 112 (FIGS. 1 and 3-8). In some embodiments, the capsule 112 is a replaceable unit that may be removably supported by the base unit 110. The capsule 112 may also be referred to as a refill unit, as a cup or other container, as a pod, or as another term. The system 100 may additionally include a volatile substance member 114 that is contained within capsule 112. The volatile substance member 114 may include or contain or otherwise comprise a volatile substance, such as a fragrant substance, essential oil, or perfume. The term "volatile substance" as used herein will be understood broadly to include substances that readily vaporize and/or move into an airstream flowing through the capsule 112 at normal ambient temperatures. As represented in FIGS. 1 and 4 and as will be described in detail, the system 100 may operate with the base unit 110 driving airflow (represented by arrow 116) through the capsule 112. The airflow 116, therefore, may carry the volatile substance from the member 114 and distribute it throughout the air outside the capsule 112.

Referring now to FIGS. 1, 2, and 4, the base unit 110 will be discussed in detail according to example embodiments. The base unit 110 may include a housing 122. The housing 122 may be a relatively thin-walled or shell-like rigid structure constructed from one or more pieces. The piece(s) of the housing 122 may define an outer side member 124, a bottom member 130, and an inner member 134.

The outer side member 124 may be frusto-conic in shape and substantially centered about the longitudinal axis 106. The outer side member 124 may taper outward in width as the outer side member 124 extends from the upper end 102 toward the lower end 104. The outer side member 124 may have a rounded (e.g., circular, ovate, etc.) cross section taken perpendicular to the axis 106. The outer side member 124 may support a user interface, such as a switch 126 and/or an indicator 128 (e.g., a display, a speaker, etc.). In some embodiments, a user may use the switch 126 to turn the system 100 ON and/or OFF. Also, the indicator 128 (e.g., display, etc.) may output information about operation of the system 100. For example, the indicator 128 may indicate the ON state and/or the OFF state of the system 100.

The bottom member 130 of the housing 122 may be rounded and bowl-shaped. The bottom member 130 may be fixedly attached to the outer side member 124 of the housing 122 proximate the lower end 104. The bottom member 130 may include a relatively flat or otherwise supportive bottom surface for standing the bottom base unit 110 upright. The bottom member 130 may have a rounded cross section taken perpendicular to the longitudinal axis 106. In some embodiments, the width of the bottom member 130 (measured perpendicular to the axis 106) and the shape of the bottom member 130 may be configured for certain uses and environments. For example, the bottom member 130 may be sized and shaped to fit within a standard vehicle cupholder. Thus, the rounded shape and relatively small width may allow the base unit 110 to be received in the cup holder and the system 100 can freshen air within a vehicle.

The bottom member 130 may also include a plurality of apertures 132 (first apertures or inlet apertures). The apertures 132 may be elongate slots that extend through the thickness of the bottom member 130. In some embodiments, the apertures 132 may provide an inlet passage for the airflow 116 into the base unit 110.

The inner member 134 of the housing 122 may define a receptacle 136 of the housing 122. the receptacle 136 may be open at the upper end 102. The receptacle 136 may extend from the outer side member 124, and the receptacle 136 may be recessed from the upper end 102 toward the lower end 104 along the axis 106. The receptacle 136 may be centered about the axis 106. The receptacle 136 may be shaped and sized according to the capsule 112. Thus, in some embodiments, the receptacle 136 may be cup-shaped and rounded for receiving the capsule 112. The depth of the receptacle 136 may be sufficient to receive the majority of the capsule 112. For example, as shown in FIGS. 1 and 4, the receptacle 136 may be deep enough such that capsule 112 is nested with the upper rim of the capsule 112 remaining exposed. The receptacle 136 may also be referred to as a docking station for the capsule 112.

The receptacle 136 may be defined by an upper rim 138, which is attached to the outer side member 124 proximate the upper end 102. The upper rim 138 may include an inner ledge 140, which may extend substantially perpendicular to the axis 106 and inward radially toward the axis 106. The inner ledge 140 may be annular and may extend about the axis 106. The receptacle 136 may also include a side wall 142, which may be cylindrical and which may depend downward along the axis 106 from the ledge 140. Additionally, the receptacle 136 may be defined by a lower support 144. The lower support 144 may extend transverse to the axis 106 and may be attached to the lower end of the side wall 142. The lower support 144 may include an outer ledge 145 projecting inward radially slightly from the lower end of the side wall 142, a disc-shaped central support member 146, and a plurality of elongate support members 148 that attach the central support member 146 to the outer ledge 145. The elongate support members 148 may radiate away from the central support member 146 and may be spaced apart equally circumferentially about the axis 106. As shown in FIG. 2, there may be three elongate support members 148 that are spaced apart approximately one-hundred-twenty degrees) (120° from each other about the axis 106.

The base unit 110 may further include a conduit opening that is proximate the receptacle 136, such as an air outlet 150. The air outlet 150 may be defined by and may be included in the lower support 144. In some embodiments, air outlet 150 may be substantially arcuate, with the elongate support members 148 extending transversely across the air outlet 150. In some embodiments, the elongate support members 148 may sub-divide the air outlet 150, and the sub-divided units of the air outlet 150 may be defined circumferentially between neighboring pairs of the plurality of elongate support members 148. These sub-units may be defined radially between the central support member 146 and the outer ledge 145. The sub-units of the air outlet 150 may be arch-shaped in some embodiments. The air outlet 150 may be in fluid communication with the apertures 132 of the bottom member 130 such that the airflow 116 may move through the base unit 110. Thus, as will be discussed, the air outlet 150 may blow air out of the base unit 110, upward along the axis 106, and into the capsule 112 in a downstream flow direction through the capsule 112.

The base unit 110 may further include one or more projections 152 (FIGS. 2 and 4). The projections 152 may be elongate rods, pins, or similar structures that are fixed at one end to the central support member 146 and that extend freely upward along the axis 106. In some embodiments, there may be a plurality (e.g., four) projections 152 that are spaced evenly about the outer radial edge of the central support member 146.

The base unit 110 may further include a fan 154. The fan 154 may be supported for rotation within the housing 122. For example, the fan 154 may be mounted beneath the lower support 144 of the housing 122. In some embodiments, the fan 154 may be substantially covered by (and protected by) the central support member 146 of the housing 122. The fan 154 may be supported for rotation about the axis 106 in some embodiments and may draw air into the base unit 110 via the apertures 132 and blow air out of the air outlet 150, generally along the axis 106. The fan 154 may be spaced vertically upward along the axis 106 from the bottom member 130 and the apertures 132 therein to draw air into the base unit 110. As represented by the illustrated embodiment, the fan 154 may be configured for positive displacement relative to the capsule 112 such that the fan 154 drives (blows) the airflow 116 into the capsule 112. However, it will be appreciated that the fan 154 of the system 100 may be configured for negative displacement relative to the capsule 112 such that the fan 154 drives (sucks) air through the capsule 112.

As will be discussed in detail below, certain features of the system 100 increase the operational efficiency of the fan 154 such that the airflow 116 may be effectively utilized for distributing the volatile substance within the capsule 112. Accordingly, the fan 154 may be compact and may have relatively low power requirements. This also enables the fan 154 to be battery powered. Such batteries can be housed within the housing 122 of the base unit 110.

In some embodiments, the base unit 110 may include a controller 158, which may be housed within the housing 122. The controller 158 may be of a variety of types and may have a wide range of capabilities without departing from the scope of the present disclosure. In some embodiments, the controller 158 may include a processor, a memory device, sensor(s), and/or other components of a known computerized control system. Furthermore, the controller 158 may rely on programmed logic and sensor input for controlling one or more features of the system 100. For example, the controller 158 may be operably connected to the fan 154 for turning the fan 154 ON and OFF. In some embodiments, the controller 158 may turn the fan 154 ON and OFF intermittently according to a predetermined and preprogrammed schedule. In some embodiments, the controller 158 may cycle the fan 154 ON for short durations (e.g., a few minutes) and then OFF for an interval of between four and five hours.

Referring now to FIGS. 1 and 3-8, the capsule 112 will be discussed in detail according to example embodiments. It will be appreciated that, in the cross sectional views of FIGS. 4, 6, and 7, the area to the left of the axis 106 is taken along a plane defined by axis 106 and radial axis 109 whereas the area to the right of the axis 106 is taken along a plane defined by axis 106 and radial axis 108.

Figure 5:
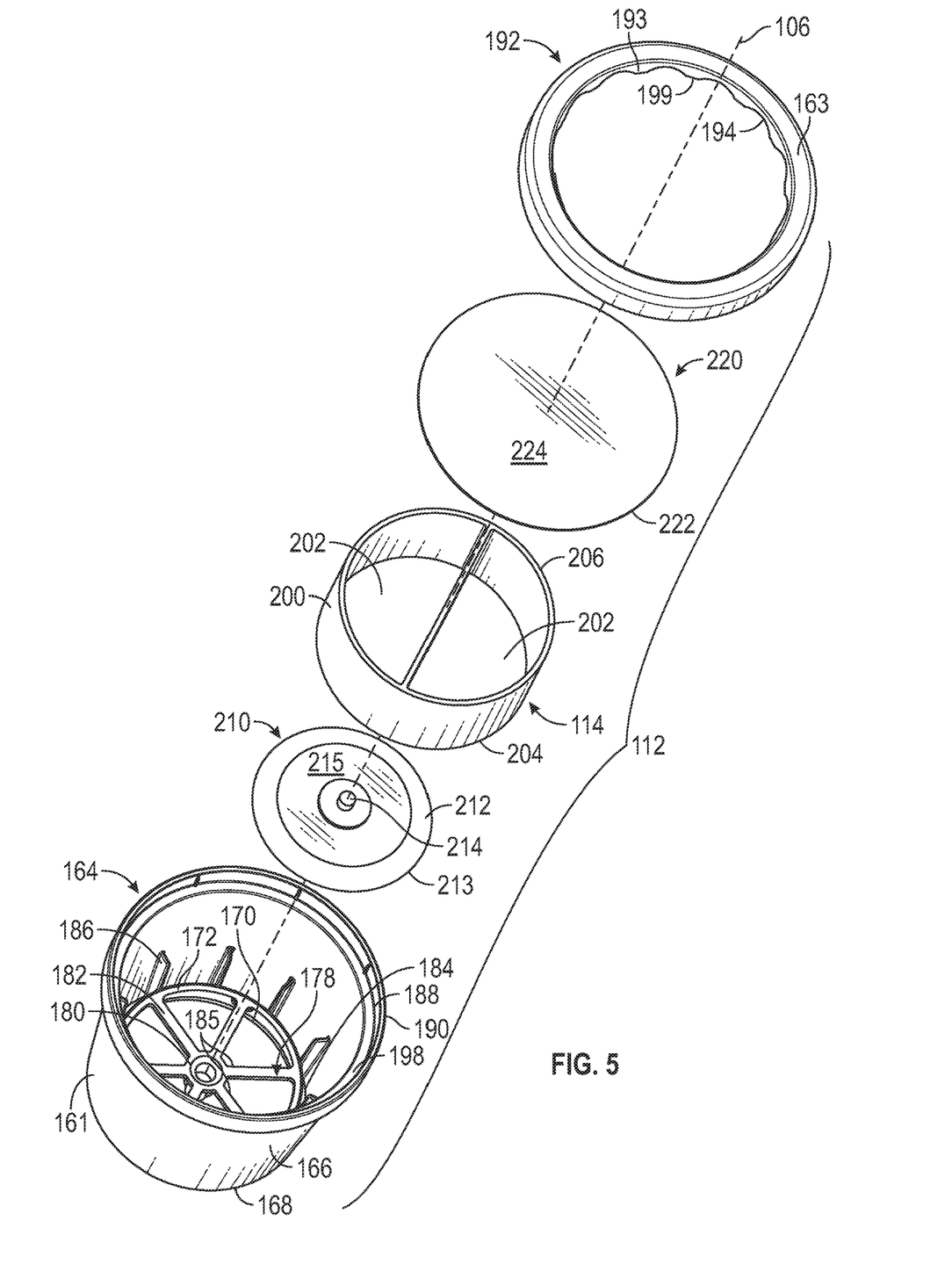
FIG. 5 is an exploded perspective view of the capsule of FIG. 3.

The capsule 112 may include a housing 162, which houses the volatile substance member 114. In some embodiments, the capsule 112 may also include one or more seal members, which regulate airflow through the capsule 112. For example, as shown in the illustrated embodiments, the capsule 112 may include a first seal member 210 and a second seal member 220.

The housing 162 may be hollow and cup-shaped. In some embodiments, the housing 162 may be substantially cylindrical and may have a generally circular cross section taken normal to the axis 106. The housing 162 may be centered on the axis 106 and may extend along the axis 106 between a first end 161 (i.e., a bottom or inlet end) and a second end 163 (i.e., a top or outlet end). The first end 161 may be disposed proximate the lower end 104 and the second end 163 may be disposed proximate the upper end 102 when mounted on the base unit 110.

As shown in FIG. 5, the housing 162 may generally include a cup member 164 and a retainer member 192. The cup member 164 and retainer member 192 may cooperate to retain and house the volatile substance member 114 as well as the one or more seal members 210, 220.

Figure 7:
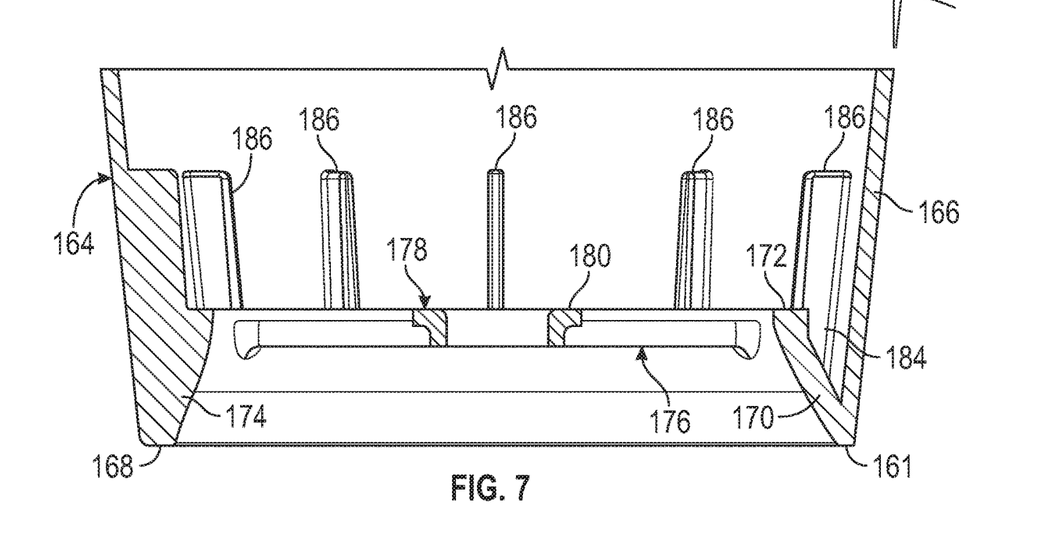
FIG. 7 is a section side view of part of a housing of the capsule of FIG. 3.

The cup member 164 may be a unitary member made of a polymeric material. The cup member 164 may include an outer wall 166 that extends circumferentially about the longitudinal axis 106. The outer wall 166 may be centered on the axis 106. The outer wall 166 may also extend along the longitudinal axis 106 in a first direction (downward) toward the first end 161 and may terminate at a first terminal end 168 of the capsule 112. The outer wall 166 may also include an upper rim 188, which is spaced apart longitudinally from the first terminal end 168 of the capsule 112. The outer wall 166 may have a circular cross section taken normal to the axis 106. The outer wall 166 may be frustoconic and tapered slightly with respect to the axis 106. As such, the outer wall 166 proximate the first end 161 may be narrower than the outer wall 166 proximate the second end 163. As shown in FIG. 7, the outer wall 166 may have a taper angle 107. Specifically, the outer wall 166 may extend substantially vertically and along the axis 106, but at the taper angle 107 with respect to the axis 106. The taper angle 107 may vary along the longitudinal height of the outer wall 166 (i.e., between the first end 161 and the second end 163). In some embodiments, the taper angle 107 may be, at most fifteen degrees)(15° with respect to the axis 106.

Figure 6:
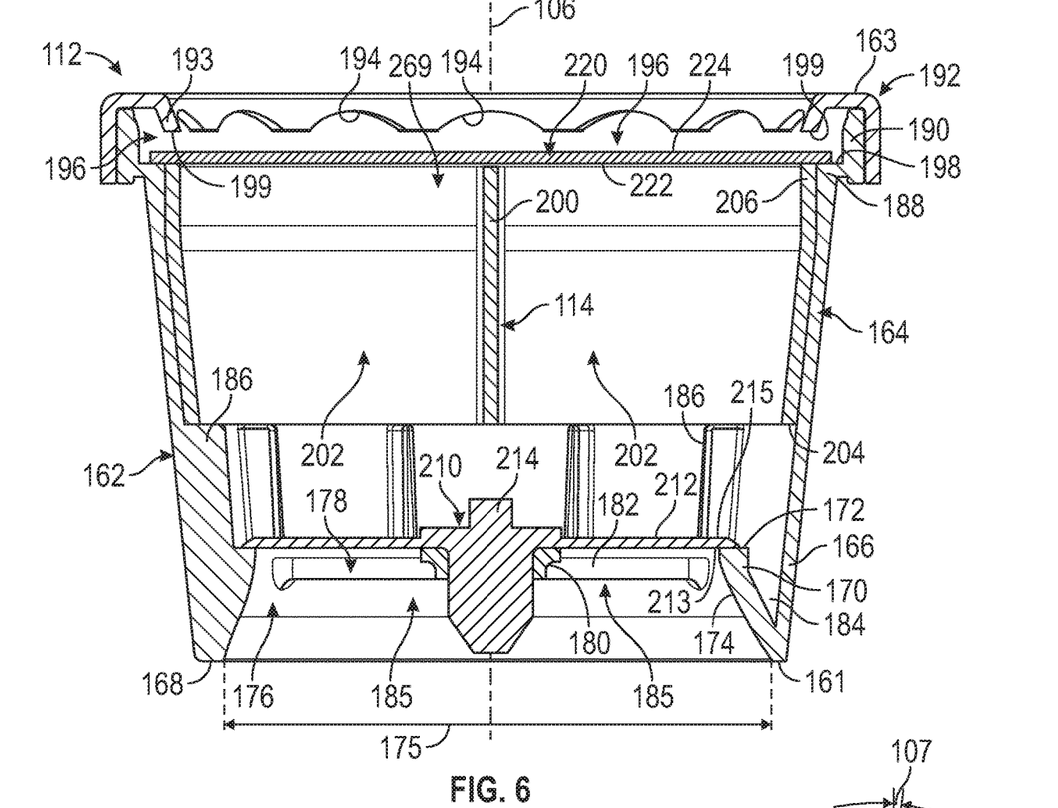
FIG. 6 is a section side view of the capsule of FIG. 3.

As shown in FIGS. 4, 6, and 7, the cup member 164 may further include an inner wall 170. The inner wall 170 may extend generally away from the first terminal end 168 in a second direction (upward) along the longitudinal axis 106 and may terminate at a first seal surface 172. The inner wall 170 may extend at an angle and/or contour slightly inward toward the axis 106 as the inner wall 170 extends away from the first terminal end 168. The inner wall 170 may be arcuate (e.g., annular) and may extend circumferentially about the axis 106. Thus, the inner wall 170 may be circular and may continuously encircle the axis 106 in some embodiments.

The inner wall 170 may include an inlet surface 174 that faces the axis 106 and that extends about the axis 106 in the circumferential direction. The inlet surface 174 may have a predefined shape or profile for directing the airflow 116 into and through the capsule 112. One example cross-sectional profile (taken along the axis 106) is shown in FIG. 7. As shown, the inlet surface 174 may have a tapered and/or contoured profile. This tapered and contoured profile may be defined in the longitudinal direction between the terminal end 168 and the first seal surface 172.

The inlet surface 174 and the first seal surface 172 may cooperate to define a first port, such as an inlet port 176, of the housing 162. The inlet surface 174 and, thus, the inlet port 176 may have a circular cross section taken normal to the axis 106.

In some embodiments, the inlet surface 174 may be tapered inward radially with respect to the axis 106. More specifically, the inlet port 176 may have a width 175 (FIG. 6) that is measured normal to the axis 106 between opposite sides of the port 176, and the width 175 of the inlet surface 174 may gradually reduce moving away from the terminal end 168 along the axis 106 toward the second end 163. The width 175 may gradually reduce along a majority of the longitudinal length of the inlet surface 174 from the terminal end 168 to the first seal surface 172. In some embodiments, the profile of the inlet surface 174 may be convexly curved with respect to the longitudinal axis 106 as shown in FIGS. 6 and 7. The inlet surface 174 may be three-dimensionally contoured (contoured longitudinally and circumferentially with respect to the axis 106). In some embodiments, at least part of the inlet surface 174 may be contoured similar to an inner diameter surface of a bell. Accordingly, the inlet port 176 may direct the airflow 116 inward radially with respect to the longitudinal axis 106 and toward the volatile substance member 114.

Figure 8:
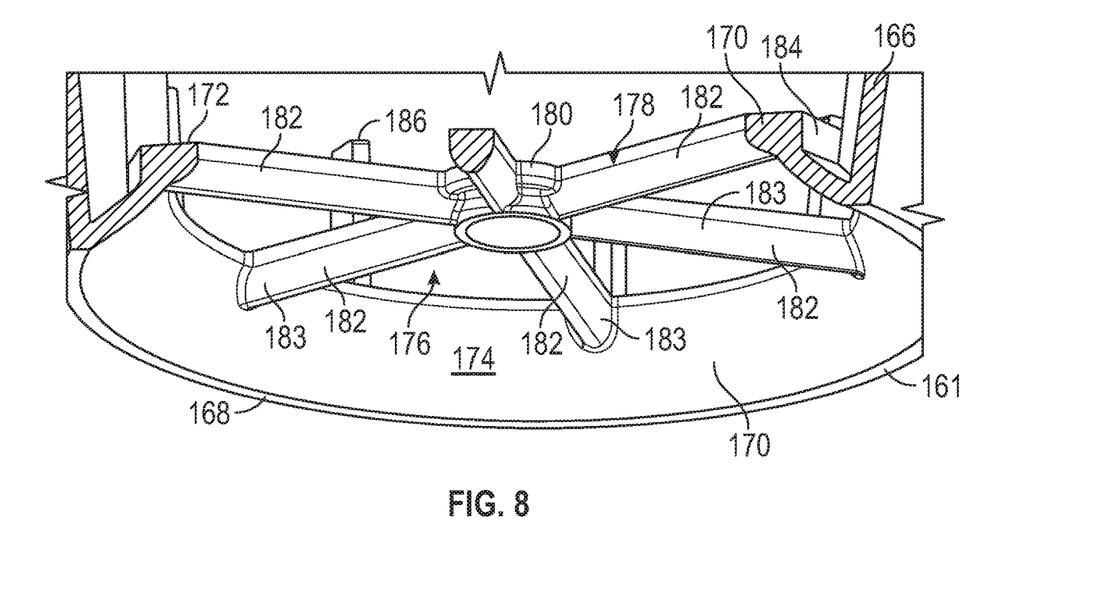
FIG. 8 is a perspective view of the part of the housing of FIG. 7.

The cup member 164 may further include a lower support 178 proximate the seal surface 172. The lower support 178 may include a disc-shaped central support member 180 and a plurality of elongate support members 182, which extend between and attach the central support member 180 to the inner wall 170. The elongate support members 182 may radiate from the central support member 180 and may be spaced equally about the longitudinal axis 106. As shown in FIG. 8, there may be six elongate support members 182. Also, as shown, the elongate support members 182 may include contoured or otherwise shaped underside surfaces 183. The underside surfaces 183 may face out of the port 176 and may be tapered and/or wedge shaped so as to gradually increase in width moving along the axis 106 toward the terminal end 168. Also, the elongate support members 182 may extend normal to the longitudinal axis 106 and across the inlet port 176 so as to subdivide the inlet port 176 into a plurality of inlet openings 185. As shown in FIGS. 5 and 8, the inlet openings 185 may be triangular or wedge-shaped, may have equal sizes, and may radiate radially and circumferentially about the axis 106.

The upper part of the inner wall 170 and the outer wall 166 may be spaced apart radially as shown in FIGS. 6-8. As such, an internal receptacle 184 may be defined between the inner wall 170 and the outer wall 166. This internal receptacle 184 may be useful for collecting condensation, debris, or other material within the capsule 112 before it falls or drips out of the capsule 112.

The cup member 164 may further include one or more inner staging flanges 186 (FIG. 5). The inner staging flanges 186 may project inward radially from the outer wall 166 and may extend along the longitudinal axis 106. There may be a plurality of inner staging flanges 186 arranged circumferentially about the axis 106. The inner staging flanges 186 may cooperatively support the volatile substance member 114 as will be discussed.

The outer wall 166 of the housing 162 may also include the upper rim 188 proximate the second end 163. A retainer ring 190 may be affixed to the upper rim 188 of the housing 162. The retainer ring 190 may encircle the upper rim 188. As shown in FIG. 6, the retainer ring 190 may project outward radially and upward longitudinally from the outer wall 166.

Referring now to FIG. 5, the retainer member 192 will be discussed. The retainer member 192 may be a unitary member. The retainer member 192 may be made of a polymeric material. The retainer member 192 may be an annular structure. The retainer member 192 may be removably attached to the retainer ring 190 of the cup member 164. As shown in FIG. 6, the retainer member 192 may clip over and receive the retainer ring 190. The retainer member 192 may be interference fit, friction fit, adhesively attached, or otherwise fixedly attached to the cup member 164. Furthermore, the retainer member 192 may include an inner rim 193 that is disposed inward radially with respect to the retainer ring 190. The inner rim 193 may depend from outer areas of the retainer member 192. The inner rim 193 may include a plurality of apertures 194. In some embodiments, the inner rim 193 may be scallop-shaped notches, grooves, cut-outs, etc. It will be appreciated that the apertures 194 may be through-holes that extend through the inner rim 193 in some embodiments.

The retainer member 192, the retainer ring 190, and the upper rim 188 of the housing 162 may cooperate to define a second port, such as an outlet port 196, of the capsule 112. Generally, the outlet port 196 may be an annular opening or space between the retainer member 192, the retainer ring 190, and the upper rim 188. The outlet port 196 may be substantially centered on and may extend circumferentially about the axis 106. A first seal surface 198 is defined on the upper rim 188 of the housing 162 and partly defines the outlet port 196. Areas of the retainer member 192 between the scallop-shaped apertures 194 define second seal surfaces 199 as shown in FIGS. 5 and 6 and define other portions of the outlet port 196. Flow through the outlet port 196 will be discussed in greater detail below.

The volatile substance member 114 is shown in FIGS. 4, 5, and 6 according to example embodiments. The volatile substance member 114 in some embodiments may include a substrate 200 with a volatile substance absorbed thereon. For example, the substrate 200 may be made from a sheet of material (e.g., cotton, paper, non-woven material, etc.) with fragrance oil absorbed thereon. Accordingly, the volatile substance member 114 may be substantially dry and moisture-free inside the capsule 112 during normal consumer use to avoid any spillage or leakage of fragrance oil. In other embodiments, the volatile substance member 114 and/or the substrate 200 may comprise beads, particles, etc. that are scented with a fragrance oil. In further embodiments, the volatile substance member 114 may include a container for a fragrant gel, fragrance oil, a wick, or other features without departing from the scope of the present disclosure.

As shown in FIG. 5, the substrate 200 may be formed to define a first side 204 and a second side 206 and one or more through-ways 202 that are defined through the volatile substance member 114 along the axis 106 from the first side 204 to the second side 206. The first side 204 may face the lower end 104, and the second side 206 may face the upper end 102. At least part of the substrate 200 may extend about the axis 106 and/or at least part of the substrate 200 may extend transverse to (e.g., radially across) the axis 106. In other embodiments (e.g., FIG. 10), the volatile substance member 114 may be star-shaped with any number of points. The volatile substance member 114 may also be heart shaped, rectangular, triangular, or shaped otherwise. As shown in FIG. 5, the first side 204 and the second side 206 may be open for receiving the airflow 116 via the throughways 202. There may be a relatively high amount of exposed surface area for passing the volatile substance to the airflow 116. The volatile substance member 114 may be enclosed and housed within housing 162 of the capsule 112. Specifically, as shown in FIG. 6, the first side 204 of the volatile substance member 114 may be supported atop the plurality of inner staging flanges 186. In additional embodiments, there may be a permeable lower support (e.g., a mesh screen) that extends horizontally across the capsule 112, that is supported on the flanges 186, and that supports the first side 204 of the volatile substance member 114. The second side 206 may be disposed slightly below the upper rim 188 of housing 162 in the position of FIG. 6.

Referring now to FIGS. 4-6, the first seal member 210 will be discussed according to example embodiments. The first seal member 210 may comprise a so-called umbrella seal in some embodiments; however, the first seal member 210 may be a check valve or another type. As shown, the first seal member 210 may be disc-shaped with a central portion 214 that is centered on the axis 106 and a thinner outer portion 212 that radiates from the central portion 214. The first seal member 210 may also include an underside 213 and a top side 215. The first seal member 210 may be supported by and attached to the housing 162. For example, the central portion 214 may be fixedly received in the central support member 180 of the lower support 178. The first seal member 210 may be made from flexible and resilient polymeric material in some embodiments. Thus, the first seal member 210 may be resiliently flexible between a first, sealed position (FIG. 6) and a second, unsealed position (FIG. 4). In the sealed position, the underside 213 may seal against the first seal surface 172 to define an annular, substantially hermetic seal therebetween. Alternatively, the underside 213 of the seal member 210 may be resiliently flexed upward and spaced apart at a distance away from the first seal surface 172 when the seal member 210 is in the unsealed position. The first seal member 210 may be biased toward sealed position. The first seal member 210 may, therefore, selectively seal the port 176 of the capsule 112 and may selectively close and open the fluid inlet of the capsule 112 as will be discussed in greater detail below, and the first seal member 210 may be referred to as an inlet seal.

With continuing reference to FIGS. 4-6, the second seal member 220 will be discussed according to example embodiments. The second seal member 220 may be disc-shaped. The second seal member 220 may be circular in some embodiments. The second seal member 220 may be made from a polymeric material, such as a flat sheet of polypropylene having a small thickness (e.g., approximately 0.015-inch thickness). However, the second seal member 220 may be an umbrella seal, a check valve, or other type in additional embodiments. The second seal member 220 may include an underside 222 and a top side 224. The second seal member 220 may be supported for floating movement by the housing 162 of the capsule 112. The second seal member 220 may be supported for movement between a first, sealed position (FIG. 6) and a second, unsealed position (FIG. 4). The underside 222 may seal against the first seal surface 198 when the second seal member 220 is in the sealed position. Alternatively, the top side 224 may be supported against the second seal surface 199 when the second seal member 220 is in the unsealed position. Accordingly, the first seal surface 198 may limit movement of the second seal member 220 along the longitudinal axis 106 in one direction, and the second seal surface 199 may limit movement of the second seal member 220 along the longitudinal axis 106 in the opposite direction. The second seal member 220 may be retained radially by the retainer member 192.

The second seal member 220 may be biased toward the sealed position. The second seal member 210 may, therefore, selectively seal the port 196 of the capsule 112 and may selectively close and open the fluid outlet of the capsule 112 as will be discussed in greater detail below, and the second seal member 220 may be referred to as an outlet seal.

When the capsule 112 is separated and removed from the base unit 110 (FIG. 6) the first seal member 210 may be biased toward its sealed position to seal the inlet port 176, and the second seal member 220 may be biased toward its sealed position to seal the outlet port 196. Accordingly, the volatile substance member 114 may be substantially encapsulated and sealed within the capsule 112.

The capsule 112 may be placed on and may be engaged with the base unit 110 (FIG. 4). Specifically, the capsule 112 may be manually oriented and rotated about the axis 106 so as to align the openings 185 with the projections 152. Then, the capsule 112 may be directed along the axis 106 and into the receptacle 136. As shown in FIG. 4, the taper dimension of the outer wall 166 of the capsule 112 may substantially correspond to the taper dimension of the side member 124 of the base unit 110 such that the outer wall 166 lies against and snugly nests on the side member 124 of the base unit 110. Also, the size and shape of the circular terminal end 168 of the capsule 112 may correspond to that of the outer ledge 145 of the base unit 110 such that the terminal end 168 snugly fits and nests on the outer ledge 145 of the base unit 110. Accordingly, the capsule 112 and the receptacle 136 may correspond in shape and size. Both the receptacle 136 and the housing 162 of the capsule 112 may be cup-shaped with rounded (e.g., circular) cross sections taken normal to the axis 106. Both the receptacle 136 and the capsule 112 may be aligned and centered on the axis 106 with corresponding widths (i.e., diameters) and tapered surfaces. As such, the capsule 112 may nest within the receptacle 136 and may be secured therein.

Furthermore, as shown in FIG. 4, an airflow fluid coupling 149 may be established between the capsule 112 and the base unit 110 as a result of the capsule 112 engaging with the base unit 110. Specifically, the air outlet 150 of the base unit 110 may fluidly connect to the inlet port 176 of the capsule 112 when the capsule 112 is supported within the receptacle 136. Placement of the capsule 112 on the base unit 110 may coincidentally fluidly connect and align the inlet port 176 to the air outlet 150. In some embodiments, the inlet port 176 covers over an entirety of the air outlet 150 of the base unit 110. Stated differently, the inlet port 176 surrounds of the base unit 110 with respect to the axis 106 (e.g., the inlet port 176 encircles the air outlet 150). Also, the terminal end 168 seats against the outer ledge 145 to block leakage flow between the outside of the capsule 112 and the base unit 110. In this position, the receptacle 136, the air outlet 150, the first end 161 of the capsule 112, the inlet port 176, the second end 163, and the outlet port 196 may be centered with respect to the longitudinal axis 106. Also, in this position, the air outlet 150, and the inlet port 176 may be substantially aligned along the longitudinal axis 106.

As the capsule 112 is seated on the base unit 110, the projections 152 may be received within the inlet openings 185 as shown in FIG. 4. If there is misalignment of the projections 152 and the inlet openings 185, then the tapered underside surfaces 183 of the elongate support members 182 may contact the projections 152. The tapering of the surfaces 183 may cause the capsule 112 to rotate about the axis 106 relative to the base unit 110 and provide alignment. As the projections 152 are received, the projections 152 may push and flex the first seal member 210 away from the sealed position and support the first seal member 210 in the unsealed position. Accordingly, placement of the capsule 112 in the base unit 110 may coincidentally unseal the inlet port 176. In some embodiments, the capsule 112 may be configured for drop-in placement within the receptacle 136 of the base unit 110, such that the force of gravity is sufficient to seat and retain the capsule 112 on the base unit 110 with the first seal member 210 unsealed. In other embodiments, slight manual force is necessary to push the capsule 112 on the base unit 110. Conversely, the capsule 112 may be manually lifted and removed from the base unit 110 easily (without having to facture or permanently deform the base unit 110 or the capsule 112).

With the capsule 112 seated and nested in the receptacle 136 and the fan 154 in the OFF state, the first seal member 210 may be supported in the unsealed position, whereas the second seal member 220 may be supported in the sealed position.

Then, the fan 154 may be turned ON by the controller 158 either manually with the switch 126 or automatically by the controller 158 according to programmed logic. The fan 154 may draw air into the inlet apertures 132 and blow the air out of air outlet 150. The airflow 116 may be received and directed by the inlet surface 174 of inlet port 176 and into the housing 162 of the capsule 112. The inlet surface 174 may direct the airflow 116 at the outward radial boundary in an inward radial direction as the airflow 116 moves into the capsule 112. The tapered underside surfaces 183 of the elongate support members 182 may also direct and focus the airflow 116 in a predetermined direction (e.g., circumferentially with respect to the axis 106). In some embodiments, the underside surfaces 183 operate similar to stators of a gas turbine engine, directing the airflow to increase efficiency of the system 100. The airflow 116 may be directed toward the underside of the first seal member 210. The underside may direct the airflow 116 outward radially as it moves downstream, and the airflow 116 may be directed into the throughways 202 of the volatile substance member 114. The airflow may, therefore, pass through the member 114 and into a so-called headspace 269 of the capsule 112 defined proximate the underside 222 of the second seal member 220. In many instances, this headspace 269 may be configured to collect airborne volatiles from the volatile substance member 114.

Initially, upon startup of the fan 154, air pressure within the capsule 112 builds to push and move (float) the second seal member 220 away from the sealed position (FIG. 6) toward the unsealed position (FIG. 4), thereby opening the outlet port 196. Accordingly, the airflow 116 at the underside 222 of the second seal member 220 may turn outward radially and turn around the outer edge of the second seal member 220 to exit the capsule 112 via the scallop-shaped apertures 194. Pressure from the airflow 116 may be sufficient to retain the second seal member 220 in the unsealed position as long as the fan 154 remains ON, thereby allowing the airflow 116 to continuously pass through the capsule 112.

Static pressure may be provided from the airflow 116 generated by the fan 154 to maintain the continuous flow path through the open inlet port 176 and the open outlet port 196. Since the first seal member 210 is mechanically opened and supported by the projections 152, the air pressure is needed instead for opening and supporting the second seal member 220. Thus, it will be appreciated that the fan 154 may be configured for operating and moving the second seal member 220. The fan 154 may be relatively light-duty and have low power consumption without compromising performance of the system 100.

It will be appreciated that the contoured and tapered surfaces of the inlet port 176 and the elongate support members 182 may direct the airflow 116 to help generate a desired and predetermined airflow 116 characteristic. In some embodiments, there may be a concentration of volatiles within known areas of the capsule 112 (e.g., in the headspace 269, especially radially near the axis 106), and the shaped inlet port 176 may direct the airflow 116 toward these areas (e.g., radially toward the axis 106. These features may also ensure that the airflow 116 applies sufficient pressure for moving the second seal member 220 from the sealed position (FIG. 6) toward the unsealed position (FIG. 4). These features may also increase exposure of the volatile substance member 114 to the airflow 116 for increasing the amount of volatile material dispersed.

When the fan 154 turns back OFF, the reduced air pressure within the capsule 112 may allow the second seal member 220 to biasingly return to the sealed position (FIG. 6). Accordingly, the second seal member 220 may be passively opened (due to pressure from the airflow 116) as well as passively closed (due to gravity, due to elasticity of the member 220, due to a spring or other biasing member, etc.). It will be appreciated that, even with the fan returning to the OFF state, the projections 152 of the base unit 110 may support the first seal member 210 in the unsealed position; however, since the inlet port 176 is covered by the base unit 110, the capsule 112 may remain substantially closed off.

In some embodiments, the controller 158 may cause the fan 154 to turn ON and OFF cyclically at predetermined intervals. Cycling the state of the fan 154 in combination with an automatically re-sealing capsule 112 may provide a number of benefits. For example, in the case of perfumes, this can reduce olfactory adaptation or "nose fatigue" of the user of the system 100. This is the phenomenon where a user is able to smell a fragrance when first exposed, but as the length of exposure increases, the consumer is no longer able to smell the fragrance. By turning off the fan 154 (and coincidentally re-sealing the capsule 112 periodically, sensory adaptation or nose fatigue is diminished.

Cycling the fan 154 ON and OFF also allows optimization of the fan's power consumption. In some embodiments, the controller 158 may cyclically operate the fan 154 such that its power consumption satisfies a predetermined Range Ratio (RR). The Range Ratio (RR) may vary according to the power cycle ratio of the fan 154 (the time ON versus the time OFF), a fan efficiency factor, and a cup loss factor. This is expressed below in equation (1):

$$\text{Range Ratio (R)} = \text{power cycle ratio} * \text{fan efficiency factor} * \text{cup loss factor} \qquad (1)$$

This is expressed in more detail below in equation (2):

$$\text{Range Ratio } (R) = \left[\frac{\text{time on, s}}{\text{time off, s}}\right] * \left[\frac{\text{air moved by fan, m}^3/\text{s}}{\text{power consumed, W}}\right] * \left[\frac{\text{air out of cup, m}^3/\text{s}}{\text{air into of cup, m}^3/\text{s}}\right] \qquad (2)$$

In some embodiments, the controller 158 may operate the fan 154 to satisfy a Range Ratio of between 1:2 to 1:14.

Moreover, the controller 158 may operate the fan 154 within a range (R1) according to equation (3):

$$\text{Range } (R1) = \frac{[\text{time off} * \text{ambient air flow} * \text{cup geometry ratio, off}]}{\left[\begin{array}{c}\text{time on} * (\text{ambient air flow} + \text{fan driven flow}) * \\ \text{cup geometry ratio, on}\end{array}\right]} \qquad (3)$$

wherein the cup geometry ratio is the area of the outlet port 196 divided by the area of the inlet port 176, wherein the cup geometry ratio approaches zero (0) when the capsule 112 is sealed, and wherein the cup geometry ratio approaches one (1) when the capsule 112 is unsealed.

Cyclically operating the fan 154 and re-sealing the capsule 112 between uses also allows for airborne volatiles within the headspace 269 to come to equilibrium, for example, when the volatile substance member 114 includes a perfume. The headspace 269 may be fully saturated with the perfume. Fragrances are made of many chemistries with different volatilities, commonly referred to as top, middle, and bottom notes. When the capsule 112 is sealed off while the fan 154 is OFF, the saturated air inside the capsule 112 is able to develop the full fragrance, including those top, middle, and bottom notes. When the fan 154 turns ON and the capsule 112 unseals, this fully saturated headspace 269 may be released, delivering the full perfume profile.

When the user decides, the capsule 112 may be lifted and manually removed from base unit 110. Once the projections 152 are outside the capsule 112, the first seal member 210 may resiliently recover and bias back toward the sealed position (FIG. 6). Accordingly, both the first and second seal members 210, 220 may be sealed, and in some embodiments, the volatile substance member 114 may be encapsulated for future use. Assuming there are multiple capsules 112 in the system, each with volatile substance members 114 of different scents, for example, these features allow the user to pick and choose which capsules 112 will be used at different times.

Figure 9:
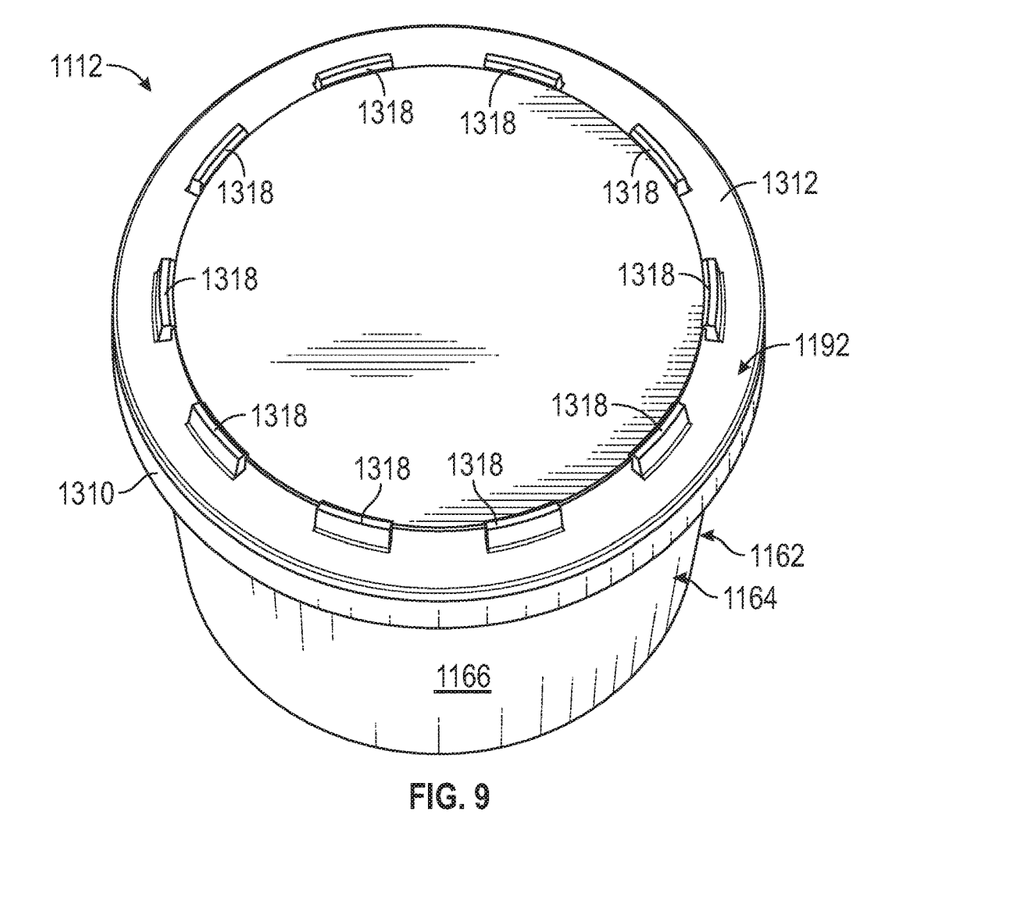
FIG. 9 is a perspective view of the capsule of the volatile substance distribution system according to additional example embodiments of the present disclosure.
Figure 10:
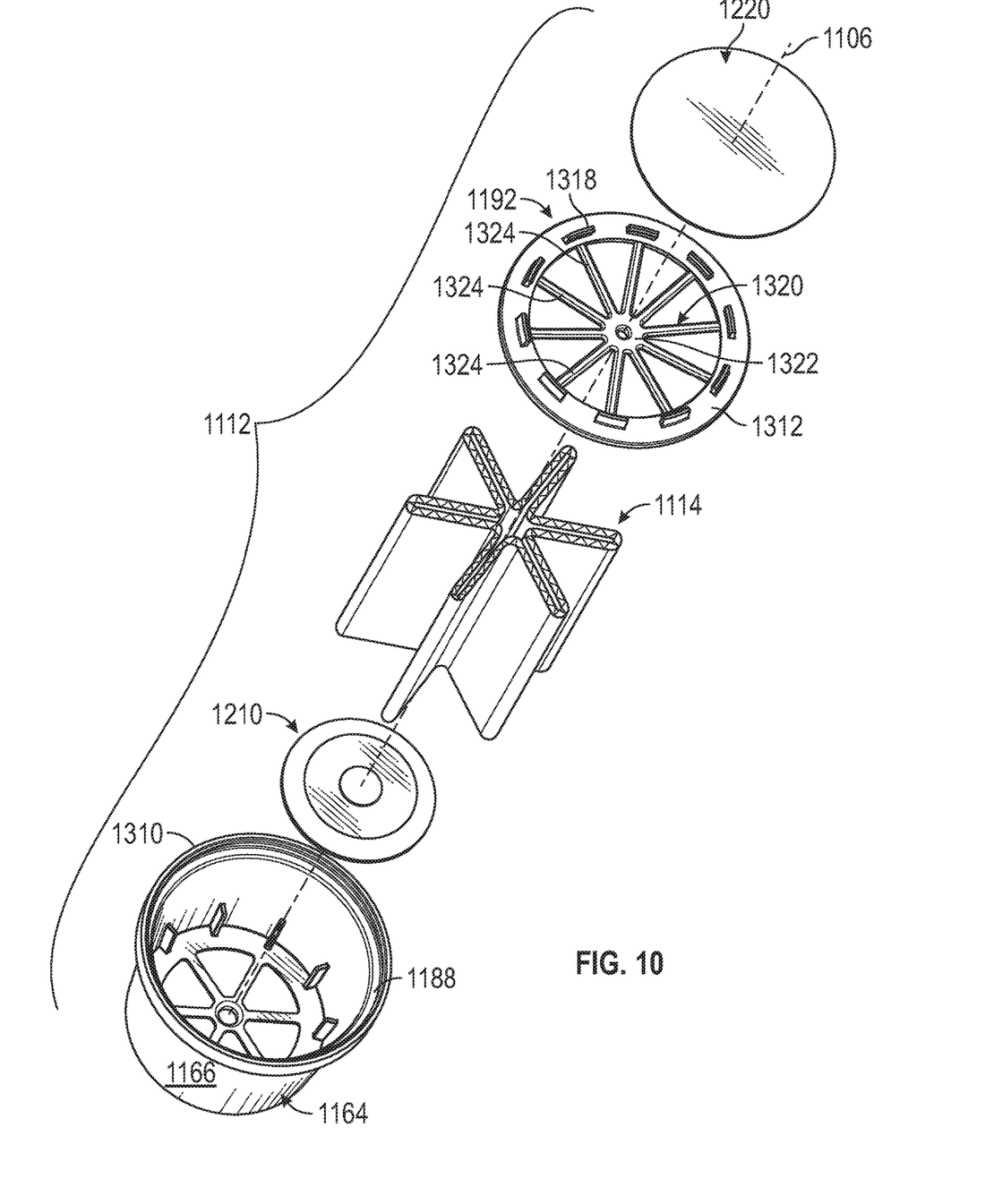
FIG. 10 is an exploded view of the capsule of FIG. 9.
Figure 11:
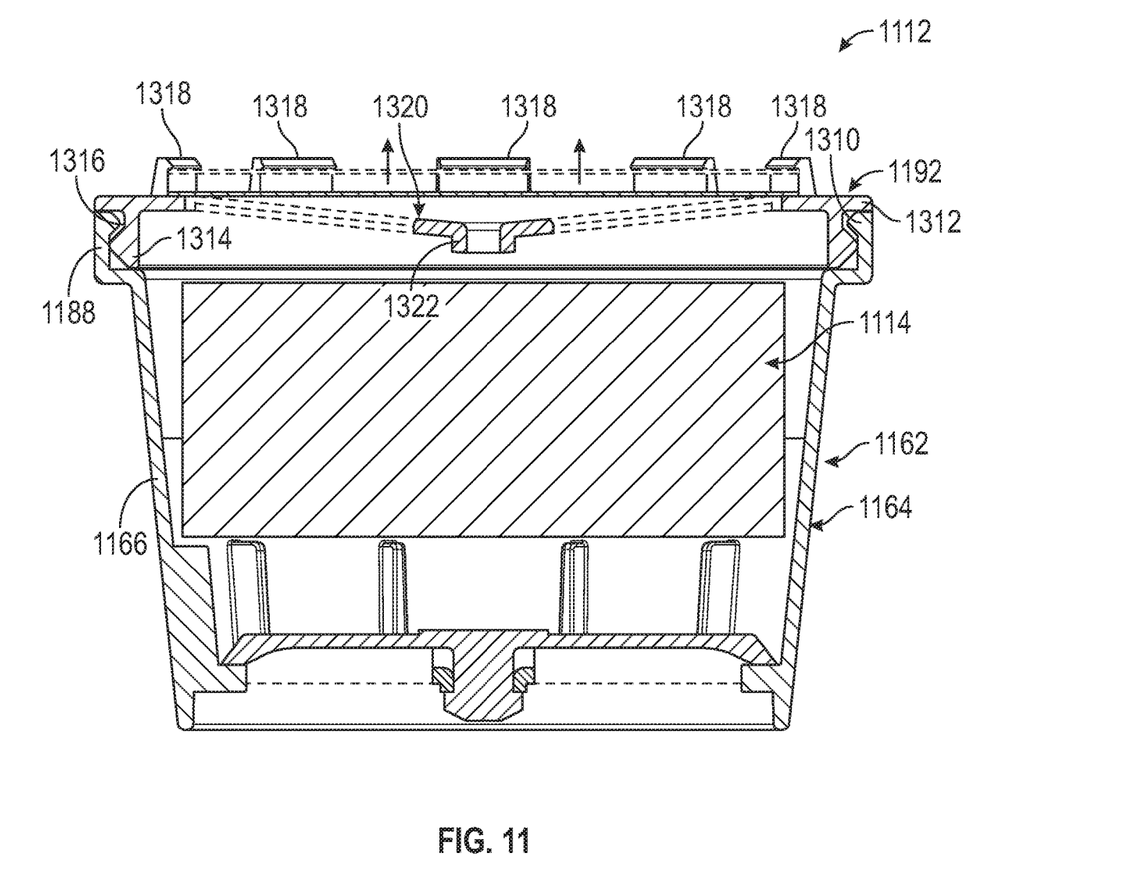
FIG. 11 is a section view of the capsule of FIG. 9.

Referring now to FIGS. 9-11, the capsule 1112 will be discussed according to additional embodiments of the present disclosure. The capsule 1112 may be used with the base unit 110 discussed above. The capsule 1112 may share several features with the capsule 112 of FIGS. 1-8; however, there may difference as discussed below. Components that correspond to those of FIGS. 1-8 are indicated with corresponding reference numbers increased by 1000.

As shown, the capsule 1112 may shaped similar and may extend along the longitudinal axis 1106. The housing 1162 may include a cup member 1164 and a retainer member 1192 as above. The capsule 1112 may also include the volatile substance member 1114. As illustrated, the volatile substance member 1114 may be star-shaped, wherein throughways are defined longitudinally through the member 1114 in a central region and between the arms of the star-shaped member 1114. As mentioned above, the volatile substance member 1114 may include a wide range of shapes without departing from the scope of the present disclosure. Furthermore, the capsule 1112 may include the first seal member 1210 and the second seal member 1220.

As shown, the upper rim 1188 of the outer wall 1166 may project outwardly radially and may include a lip 1310. The lip 1310 may be directed inward radially.

Additionally, the retainer member 1192 may include an outer flange 1312. An annular lower retainer member 1314 may project longitudinally from the underside of the outer flange 1312. An undercut 1316 may be defined in the lower retainer member 1314 and may receive the lip 1310 of the upper rim 1188 to retain the retainer member 1192 on the cup member 1164. Furthermore, the retainer member 1192 may include one or more upper retainer members 1318 that project from the top side of outer flange 1312. The upper retainer members 1318 may have a hook-shaped profile along the axis 106. The upper retainer members 1318 may be configured for limiting movement of the second seal member 1220 away from the sealed position and retaining the second seal member 1220 in the unsealed position. Also, in some embodiments, the retainer member 1192 may include a seal support structure 1320. The seal support structure 1320 is an optional feature of the capsule 1112. In some embodiments, the seal support structure 1320 may include a central support member 1322 and a plurality of elongate support members 1324. The seal support structure 1320 may support the central portion of the second seal member 1220 when in the sealed position. Other embodiments fall within the scope of the present disclosure. For example, the second seal member 1220 may be fixedly attached to the central support member 1322 and outer radial portions may resiliently flex between the sealed and unsealed positions.

Operation of the system with the capsule 1112 may be substantially the same as discussed with respect to the capsule 112 of FIG. 4. Accordingly, airflow may be driven by the base unit 110 and may be directed through the capsule 1112 for delivering the volatile substance.

Various manufacturing methods may be employed for forming the capsule 112, 1112 and the base unit 110. Some structures, such as the housing and pieces thereof may be formed from injection molding processes, from additive manufacturing processes, or otherwise. The first and/or second seal members 210, 220 may be die cut, injection molded, stamped, pressed, or made using other typical manufacturing techniques. The seal members 210, 220 may be made from plastic, film, foil, or a combination of materials. Parts may be assembled using conventional fasteners, adhesives, or otherwise. With regard to the base unit 110, the fan 154, the controller 158, and/or other components may be mounted on a support structure and then housed within the housing 122. The capsule 112 may be formed by inserting the first seal member 210, the volatile substance member 114, and the second seal member 220 in the cup member 164 and then press-fitting the retainer member 192 onto the cup member 164. In other embodiments, the second seal member 220 and the retainer member 192 may be assembled together as a unit, which is then attached to the cup member 164. In another embodiment, the retainer member 192 may be pressed onto the cup member 164, and then the second seal member 220 may be pressed into the retainer member 192.

The system 100 may vary in a number of ways without departing from the scope of the present disclosure. For example, the first and second seal members 210, 220 are optional features. It will be appreciated that the capsule 112, 1112 may include any number of seal members. Other seal members fall within the scope of the present disclosure. For example, the capsule 112, 1112 may include one or more removable and disposable seals. There may be a peel-away seal made from paper, plastic film, foil, or a combination. In some embodiments, a peel-away seal may be adhesively attached to the terminal end 168 of the housing of the capsule 112, 1112. Also, in some embodiments, the projections 152 may puncture a seal member of the capsule 112, 1112 to open the inlet port thereof. The outlet port may similarly incorporate a peel-away or other type of disposable seal. The capsule 112 may also include one or more removable caps the cover over the inlet or outlet port. Such caps may be hingeably attached to the housing or may be threadably attached to the housing 162. Furthermore, in some embodiments, the cap may be manually replaceable by a user for sealing and re-sealing the capsule 112.

In an additional example, the capsule 112 may be substantially the same except that the first seal member 210 is omitted. The second seal member 220 may be included for sealing the port at the upper end 102 (here, the outlet port 196). The inlet port 176 may remain open; however, the base unit 110 may prevent back flow from the capsule 112 and, if the capsule 112 is removed therefrom, then the user may simply place the capsule 112 on a flat surface to substantially close of the inlet port 176. The capsule 112 may also be re-sealed within secondary packaging (a bag, a clamshell container, etc.) between uses.

Accordingly, the system 100 is useful, compact, and ergonomic. The capsule 112, 1112 is easy and intuitive to engage with the base unit 110. When attached the air outlet 150 aligns with the inlet port 176, and the airflow 116 is utilized efficiently. Substantially all air flow entering the base unit 110 is blown through the capsule 112. In other words, a single, continuous flow path is defined through the base unit 110 and the capsule 112 from the apertures 132 of the base unit 110 to the outlet port 196 of the capsule 112. As such, a less expensive fan 154 may be incorporated without compromising performance. The inlet port 176 includes rounded, tapered, and/or otherwise shaped surfaces to direct the airflow 116 in a controlled and effective manner. Furthermore, the configuration of the mechanically-opened first seal member 210 encapsulates the volatile substance member 114 and, yet, is simple to unseal. Likewise, the passively-opened second seal member 220 seals the capsule 112, allows the headspace 269 to collect the volatile material, and provides other benefits.

Terms such as "first" and "second" have been utilized above to describe similar features or characteristics (e.g., longitudinal directions) in view of the order of introduction during the course of description. In other sections of this Application, such terms can be varied, as appropriate, to reflect a different order of introduction. While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the present disclosure in any way. Rather, the foregoing Detailed Description will provide those skilled in the art with a convenient road map for implementing an exemplary embodiment of the present disclosure. It is understood that various changes may be made in the function and arrangement of elements described in an exemplary embodiment without departing from the scope of the present disclosure as set forth in the appended claims.

What is claimed is:

1. A capsule for a volatile material distribution system comprising:
    a housing that extends along a longitudinal axis between a first end and a second end, the first end defining an inlet port and the second end defining an outlet port;
    a volatile substance member that includes a volatile substance, the volatile substance member contained and supported within the housing;
    an outlet seal member disposed proximate the outlet port and configured to selectively move between an unsealed position and a sealed position relative to the outlet port, the outlet seal member substantially sealing the outlet port in the sealed position, the outlet port being unsealed with the outlet seal member in the unsealed position;
    the housing, with the outlet seal member in the unsealed position, configured to receive an airflow that flows into the inlet port, past the volatile substance member, and out of the outlet port;
    wherein the outlet port is defined between a first seal surface and a second seal surface of the housing, the first seal surface and the second seal surface spaced apart along the longitudinal axis; and
    wherein the outlet seal member is configured to move along the longitudinal axis between the sealed position and the unsealed position, the first seal surface limiting movement of the outlet seal member in a first direction along the longitudinal axis, the second surface limiting movement of the outlet seal member in a second direction along the longitudinal axis.

2. The capsule of claim 1, wherein the outlet seal member is configured to passively move from the sealed position to the unsealed position due to pressure from the airflow into the capsule.

3. The capsule of claim 1, wherein the inlet port and the outlet port are substantially centered with respect to the longitudinal axis of the capsule.

4. The capsule of claim 3, wherein the inlet port and the outlet port are substantially rounded and extend about the longitudinal axis.

5. The capsule of claim 3, wherein the volatile substance member includes a substrate that defines at least one throughway for passage of the airflow through the volatile substance member; and
    wherein the at least one throughway extends along the longitudinal axis.

6. The capsule of claim 1, further comprising an inlet seal member that is supported by the housing for movement between a sealed position and an unsealed position, the inlet seal member substantially sealing off the inlet port in the sealed position, and the inlet port being open with the inlet seal member in the unsealed position.

7. The capsule of claim 1, wherein the housing of the capsule includes a plurality of scallop-shaped apertures, the second seal surface defined between adjacent pairs of the plurality of scallop-shaped apertures.

8. A volatile substance distribution system comprising:
    a base unit having a base unit housing that supports a fan and that defines an air outlet configured to direct air driven by the fan away from the base unit;
    a capsule configured to be removably supported on the base unit, the capsule including:
        a housing that extends along a longitudinal axis between a first end and a second end, the first end defining an inlet port and the second end defining an outlet port, the housing configured to move between an engaged position and a disengaged position relative to the base unit, the housing, in the engaged position, being removably supported on the base unit with the inlet port fluidly connected to the air outlet of the base unit, the housing, in the disengaged position, being spaced apart from the base unit;
        a volatile substance member that includes a volatile substance, the volatile substance member contained and supported within the housing;
        an outlet seal member disposed proximate the outlet port and configured to selectively move between an unsealed position and a sealed position relative to the outlet port, the outlet seal member substantially sealing the outlet port in the sealed position, the outlet port being unsealed with the outlet seal member in the unsealed position;
        the housing, in the engaged position and with the outlet seal member in the unsealed position, configured to receive the air from the air outlet that flows into the inlet port, past the volatile substance member, and out of the outlet port;
        wherein the outlet port is centered with respect to the longitudinal axis of the capsule and is defined between a first seal surface and a second seal surface, the first seal surface and the second seal surface spaced apart along the longitudinal axis; and
        wherein the outlet seal member is configured to move along the longitudinal axis between the sealed position and the unsealed position, the first seal surface limiting movement of the outlet seal member in a first direction along the longitudinal axis, the second surface limiting movement of the outlet seal member in a second direction along the longitudinal axis.

9. The system of claim 8, wherein the base unit includes a receptacle that is recessed along the longitudinal axis;
    wherein the air outlet is included in the receptacle and is centered with respect to the longitudinal axis;
    wherein the inlet port and the outlet port are substantially centered with respect to a longitudinal axis of the capsule when the housing is in the engaged position; and
    wherein the inlet port and the outlet port are separated at a distance along the longitudinal axis.

10. The system of claim 9, wherein the capsule is nested within the receptacle when engaged with the base unit.

11. The system of claim 9, wherein the inlet port and the outlet port are substantially rounded and extend about the longitudinal axis.

12. The system of claim 9, wherein the volatile substance member includes a substrate that defines at least one throughway for passage of the air through the volatile substance member; and
    wherein the at least one throughway extends along the longitudinal axis.

13. The system of claim 8, further comprising an inlet seal member supported by the housing of the capsule for movement between a sealed position and an unsealed position, the inlet port being substantially sealed when the inlet seal member is in the sealed position, the inlet port being open when the inlet seal member 1s in the unsealed position.

14. The system of claim 13, further comprising a controller that intermittently changes the fan between an ON state and an OFF state;
    wherein, with the capsule engaged with the base unit, the inlet seal member remains supported in the unsealed position with the fan in both the ON state and the OFF state; and wherein, with the capsule engaged with the base unit, the outlet seal member is supported in the sealed position with the fan in the OFF state; and wherein, with the capsule engaged with the base unit, the outlet seal member is supported in the unsealed position with the fan in the ON state.

15. The system of claim 14, wherein the inlet seal member is biased toward the sealed position; and wherein the outlet seal member is biased toward the sealed position.

16. The system of claim 15, wherein the inlet seal member is configured to mechanically move from the sealed position to the unsealed position as a result of engaging the capsule on the base unit; and wherein the outlet seal member is configured to passively move from the sealed position to the unsealed position due to pressure from the air moved by the fan into the capsule.

17. A method of manufacturing a volatile substance distribution system comprising:

providing a housing of a capsule that extends along a longitudinal axis between a first end and a second end, the first end defining an inlet port and the second end defining an outlet port;

providing a volatile substance member that includes a volatile substance within the housing;

supporting an outlet seal member proximate the outlet port, the outlet seal member configured to selectively move between an unsealed position and a sealed position relative to the outlet port, the outlet seal member substantially sealing the outlet port in the sealed position, the outlet port being unsealed with the outlet seal member in the unsealed position;

the housing, with the outlet seal member in the unsealed position, configured to receive air from an air outlet that flows into the inlet port, past the volatile substance member, and out of the outlet port;

wherein the outlet port is defined between a first seal surface and a second seal surface of the housing, the first seal surface and the second seal surface spaced apart along the longitudinal axis; and wherein the outlet seal member is configured to move along the longitudinal axis between the sealed position and the unsealed position, the first seal surface limiting movement of the outlet seal member in a first direction along the longitudinal axis, the second surface limiting movement of the outlet seal member in a second direction along the longitudinal axis.

18. The capsule of claim 1, wherein the outlet seal member comprises a substantially flat top side configured to abut against the first seal surface; and wherein the outlet seal member comprises a substantially flat underside configured to abut against the second seal surface.

19. The system of claim 8, wherein the outlet seal member comprises a substantially flat top side configured to abut against the first seal surface; and wherein the outlet seal member comprises a substantially flat underside configured to abut against the second seal surface.

* * * * *